United States Patent [19]

Bonnet

[11] Patent Number: 5,249,572
[45] Date of Patent: Oct. 5, 1993

[54] METHOD AND APPARATUS FOR CONTROLLING THE PACING RATE OF A METABOLIC DEMAND PACEMAKER

[75] Inventor: Jean-Luc Bonnet, Paris, France
[73] Assignee: ELA Medical, Montrouge, France
[21] Appl. No.: 813,905
[22] Filed: Dec. 23, 1991
[30] Foreign Application Priority Data
  Dec. 27, 1990 [FR] France ................... 90 16292
[51] Int. Cl.$^5$ .......................................... A61N 1/365
[52] U.S. Cl. ................................................... 607/20
[58] Field of Search ................................ 128/419 PG
[56] References Cited

U.S. PATENT DOCUMENTS

| | | | |
|---|---|---|---|
| 4,566,456 | 1/1986 | Koning et al. | 128/419 |
| 4,576,183 | 3/1986 | Plicchi | 128/419 PG |
| 4,702,253 | 10/1987 | Nappholz et al. | 128/419 |
| 4,730,619 | 5/1988 | Koning et al. | 128/419 |
| 4,884,576 | 12/1989 | Alt | 128/419 PG |
| 4,901,725 | 2/1990 | Nappholz et al. | 128/419 PG |
| 4,961,423 | 10/1990 | Canducci | 128/419 PG |
| 4,972,834 | 11/1990 | Begemann et al. | 128/419 PG |
| 5,044,365 | 9/1991 | Webb et al. | 128/419 PG |
| 5,085,215 | 2/1992 | Nappholz et al. | 128/419 PG |

FOREIGN PATENT DOCUMENTS
  178528 4/1986 European Pat. Off. .

Primary Examiner—William E. Kamm
Attorney, Agent, or Firm—Davis Hoxie Faithfull & Hapgood

[57] ABSTRACT

Controlling a cardiac pacemaker wherein the cardiac pacing rate is controlled according to a measure of the metabolic demand. The average minute ventilation MV-8-0 is measured over the eight last breathing cycles (first one to eighth one), and it is compared with the average minute ventilation MV-8-1 over the previous eight breathing cycles (ninth one to sixteenth one), and it is determined that an effort phase is present when MV-8-0>MV-8-1, and that a recovery phase is present when MV-8-0<MV-8-1. These determinations are used to determine whether sensed changes in the ventilation correspond to transitions between the effort and recovery or ventilation gaps or artifacts so that the cardiac pacing rate is not decreased during an effort.

33 Claims, 10 Drawing Sheets

--- CR calculated
— CR applied

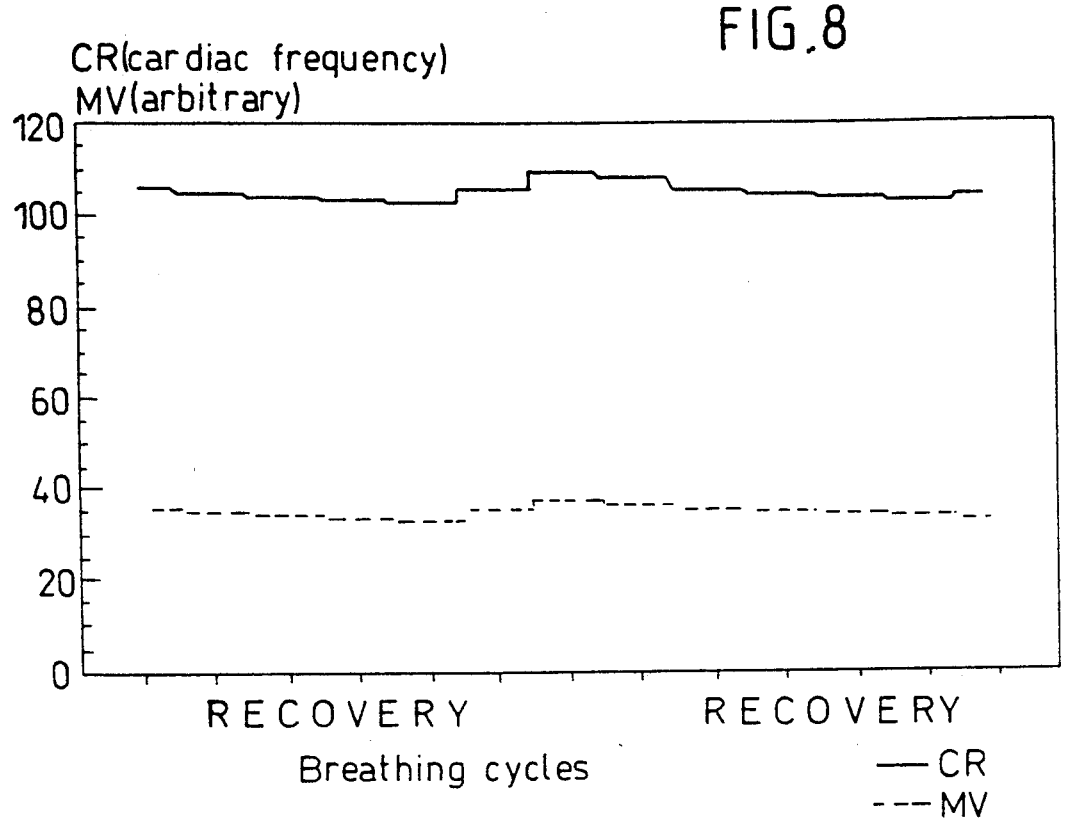
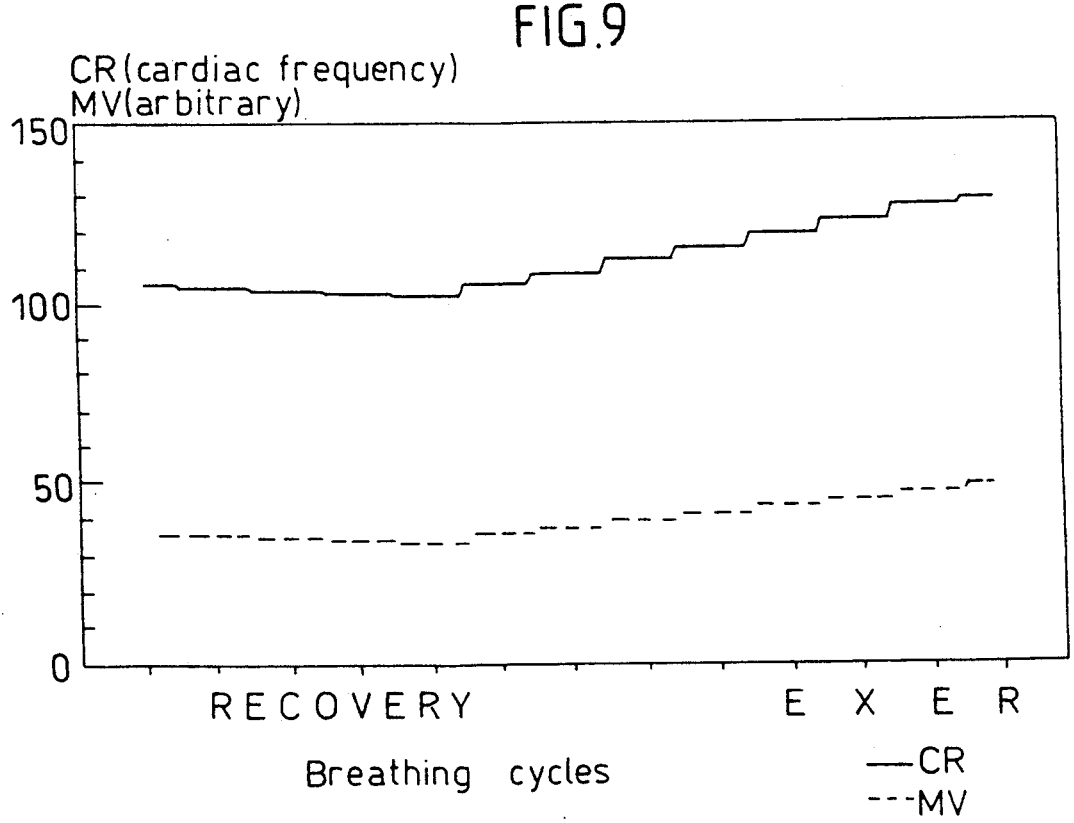

METHOD AND APPARATUS FOR CONTROLLING THE PACING RATE OF A METABOLIC DEMAND PACEMAKER

A portion of the disclosure of this patent document contains material which is subject to copyright protection. The copyright owner has no objection to the facsimile reproduction by any one of the patent disclosure, as it appears in the Patent and Trademark Office patent files or records, but otherwise reserves all copyright rights whatsoever.

FIELD OF THE INVENTION

This invention relates to controlling a pacemaker, and more particularly to controlling a metabolic demand pacemaker in which the pacing rate is controlled according to an indicator of the metabolic demand, namely according to the level of activity of the patient wearing the pacemaker.

BACKGROUND OF THE INVENTION

During a person's effort, i.e., a level of activity above a baseline activity level at rest, certain physiological parameters become modified. The relative changes in these parameters can in some instances be correlated to the level of effort and give information about the metabolic demand. Rate-adaptive metabolic demand pacemakers monitor such a physiological parameter and process parameter changes, based on a relationship between the monitored parameter and the cardiac rate, to determine a cardiac pacing rate. As used herein, the term "pacing rate" and "cardiac pacing" should be understood to mean the frequency or rate at which electrical pulses are delivered to a suitable location of the heart to stimulate a contraction. For example, the calculated cardiac rate may be controlled by an algorithm defining the relationship between the sensed parameter and the corresponding activity level. Thus, the calculated cardiac rate is controlled corresponding to the activity level represented by the physiological parameter.

In most metabolic demand pacemakers, one of these parameters is selected and monitored. A measurement of the parameter is made periodically. There is then periodically determined an increase, decrease or an upholding of the cardiac rate based on any relative change in the measured parameter.

One problem with these devices is that the parameter may have a non-negligible physiological variability from one measurement to the next. This in turn may lead to an error of interpretation about the real activity of the patient. For example, if the selected physiological parameter is the minute ventilation (also known as minute volume), namely a parameter corresponding to the air volume being expired during one minute, this parameter will present erratic variations called "ventilation gaps" during a period of effort. These ventilation gaps correspond to changes in the breathing rhythm that cause a decrease of the minute ventilation measure during a few breathing cycles.

The direct consequence in a controlled system responsive to such a parameter is a momentary decrease of the cardiac rate. This occurs, however, while the patient is still active and perhaps increasingly active, and is detrimental. Imagine not breathing while running up a flight of stairs and swimming underwater. Of particular concern is the occurrence of ventilation gaps during an effort phase which result in a decrease in the cardiac rate.

There is thus a continuing need to provide improved control of a metabolic demand pacemaker so that non-negligible physiological variations in a monitored parameter do not result in an erroneous change in the pacing rate.

SUMMARY OF THE INVENTION

It is, therefore, an object of the present invention to provide for controlling the pacing rate in response to a physiological parameter to avoid premature variations of the pacing rate.

It is another object of the invention to distinguish between sensed changes in the monitored parameter corresponding to artifacts and changes corresponding to the end of an effort or recovery phase.

It is another object of the present invention to provide an improved algorithm for correlating changes in a monitored parameter to changes in the pacing rate.

It is another object to distinguish between the case of an increase of the value of the parameter liable to lead to an increase of the cardiac rate, and the case of a decrease of the value of the parameter liable to lead to a decrease of the cardiac rate.

It is another object of the invention to minimize, if not eliminate, the occurrence of a reduction in the cardiac rate during a phase of effort.

The present invention provides improved control over the pacing rate provided by a pacemaker to correspond to the patient's effort such that a monitored parameter representative of metabolic demand is processed to avoid physiologic variations not representative of effort. Broadly, the invention concerns methods and apparatus for periodically determining a cardiac pacing rate in response to a monitored physiological parameter such that a first plurality of measures of the parameter are compared to a second plurality of measures of the parameter, and determining that an effort is increasing, decreasing or remaining the same in response to the comparison. Accordingly, the pacing rate may be adjusted in response to the determination.

One aspect of the invention is directed towards a method for controlling a metabolic demand rate responsive pacemaker wherein a calculation of the cardiac rate CR is made every nth cardiac cycle based on a monitored physiological parameter.

One such method includes:

(a) monitoring a parameter that changes in response to changes in metabolic demand;

(b) determining a first average of a first plurality of parameter measures;

(c) determining a second average of a second plurality of parameter measures, the second plurality being measured relatively later in time than the first plurality;

(d) comparing the first and second determined averages; and (e) determining that the effort is increasing in response to the first average being less than the second average and decreasing in response to the first average being greater than the second average.

In one embodiment, n may be selected from between 2 and 10 cycles, and more preferably 4 cycles, such that the cardiac rate is recalculated every four cardiac cycles. Each of the first plurality and the second plurality is selected from between 2 and 32 measures, preferably each being eight measures taken over eight parameter cycles such that the second average is of the most recent eight parameter cycles and the first average is of the eight parameter cycles preceding those used in determining the first average. The term "parameter cycle" refers to the frequency that a measure of the parameter is acquired, for example, a breathing cycle, a cardiac cycle or some selected cycle corresponding to a selected time period, depending on the physiology of the parameter. The averages are preferably sliding averages that are updated either with each new measure or with each calculation of the cardiac rate.

One preferred physiological parameter is minute ventilation having a parameter cycle that is a breathing cycle. Other parameters useful as indicators of metabolic demand, e.g., blood temperature, blood pH, and cardiac output, may be used.

In accordance with the present invention, the determination of whether an effort is continuing or whether a recovery phase has begun is based on the relationship between the two determined averages and may be used in selecting the pacing rate. More particularly, the determination may be used to select the pacing rate as one of the existing or last calculated value and the next or new calculated value.

Another method of the present invention is directed to controlling a metabolic demand rate responsive pacemaker wherein the pacing rate is periodically calculated every n cardiac cycles based on a linear control relationship with the monitored parameter. One such method comprises:

(a) monitoring the minute ventilation as the physiological parameter;
(b) determining an average of the measured minute ventilation MV-8-0 over the last eight breathing cycles, i.e., from the first to the eighth last cycles;
(c) determining an average of the measured minute ventilation MV-8-1 over the preceding eight breathing cycles, i.e., from the ninth to the sixteenth last cycles;
(d) comparing the averages MV-8-0 and MV-8-1; and
(e) determining that an effort phase exists when MV-8-0 > MV-8-1, and that a recovery phase is present with MV-8-0 < MV-8-1.

Preferably, the pacing rate is controlled in response to the measured physiological parameter, the determination of whether an effort or recovery phase exists, and the prior calculated cardiac rate. For example, the present invention advantageously provides that during a determined phase of effort, the pacing rate is maintained at its prior calculated value when a ventilation gap, corresponding to a temporary decrease of the minute ventilation, leads to the calculation of a decreasing controlled cardiac rate. After the end of the ventilation gap, the pacing rate will adjusted to be at the calculated cardiac rate at that time.

Also, during an effort phase the pacing rate is maintained at its last calculated value in the case of a decrease of the calculated cardiac rate, until the transition from an effort phase to the recovery phase is confirmed by the comparison of MV-8-0 and MV-8-1. Thereafter, in the recovery phase, the pacing rate will be adjusted to be at the calculated cardiac rate at that time.

Further, the invention provides that during the recovery phase, the cardiac pacing rate is reduced, while a deceleration slope is respected, and the last minimum controlled cardiac rate is memorized during the next four breathing cycles. This provides for the recovery phase to be maintained in the case of a ventilation artifact, indicative of renewed effort, that lasts less than four breathing cycles. If the ventilation increase continues past those four breathing cycles, then it is deemed not to be an artifact and the effort phase is resumed.

BRIEF DESCRIPTION OF THE DRAWINGS

Further features of the invention, its nature and various advantages will be more apparent from the accompanying drawings and the following detailed description of the invention, in which like reference numerals refer to like elements, and in which:

FIG. 8 is a plot comparing the calculated cardiac rate CCR and an arbitrary measure of the minute ventilation MV versus breathing cycles, during a recovery phase including a rebound of ventilation during recovery;

FIG. 9 is a plot comparing the calculated cardiac rate CCR and an arbitrary measure of the minute ventilation MV versus breathing cycles, during a transition between recovery and effort phases;

DETAILED DESCRIPTION OF THE INVENTION

Figure 1:
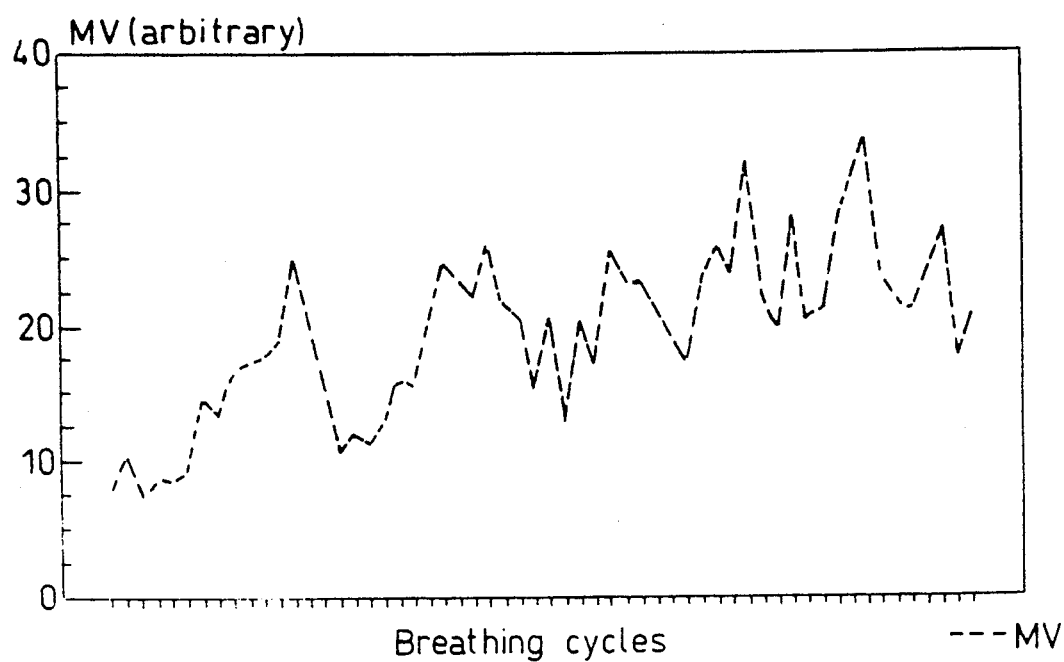
FIG. 1 is a plot of an arbitrary measure of minute ventilation MV versus a series of breathing cycles during an effort.

Referring to FIGS. 1–10, a preferred embodiment of the present invention incorporates a measure of the minute ventilation parameter. FIG. 1 illustrates an arbitrary minute ventilation MV during an effort test in response to the physiological parameter monitored by a suitable sensor. The occurrence of ventilation gaps are indicated, some of which are labeled G.

Preferably, the minute ventilation parameter is obtained by injecting a pulsatile current (e.g., 15 microsecond pulses having an amplitude of 400 microamps at a repetition rate of 8 Hz) into the heart and measuring transthoracic impedance variations using a conventional bipolar endocardial lead in the right heart, e.g., lead Model T84, available from Ela Medical, Montrouge, France, bandpass filtering out impedance signal frequencies not related to the respiratory impedance variations, and converting the respiratory impedance maximum and minimum values and frequency variations over time into volume of air per minute.

The measured value MV (also referred to as "sensed" value) is then received for processing in accordance with the present invention. Preferably, MV is calculated every mth breathing cycle as an average of the measures acquired since the last calculation such that m is selected from between 2 and 16, preferably four. Alternate calculations may be made, for example, every breathing cycle based on an average of from 2 to 16 preceding measures.

Alternate techniques for acquiring minute ventilation and selecting a calculated cardiac pacing rate may, of course, be used. See for example, U.S. Pat. Nos. 4,901,725, 4,702,253 and 4,596,251. The actual acquisition of the physiological parameter and determination of the measure of minute ventilation parameter or other physiological parameter forms no part of the present invention.

Figure 2:
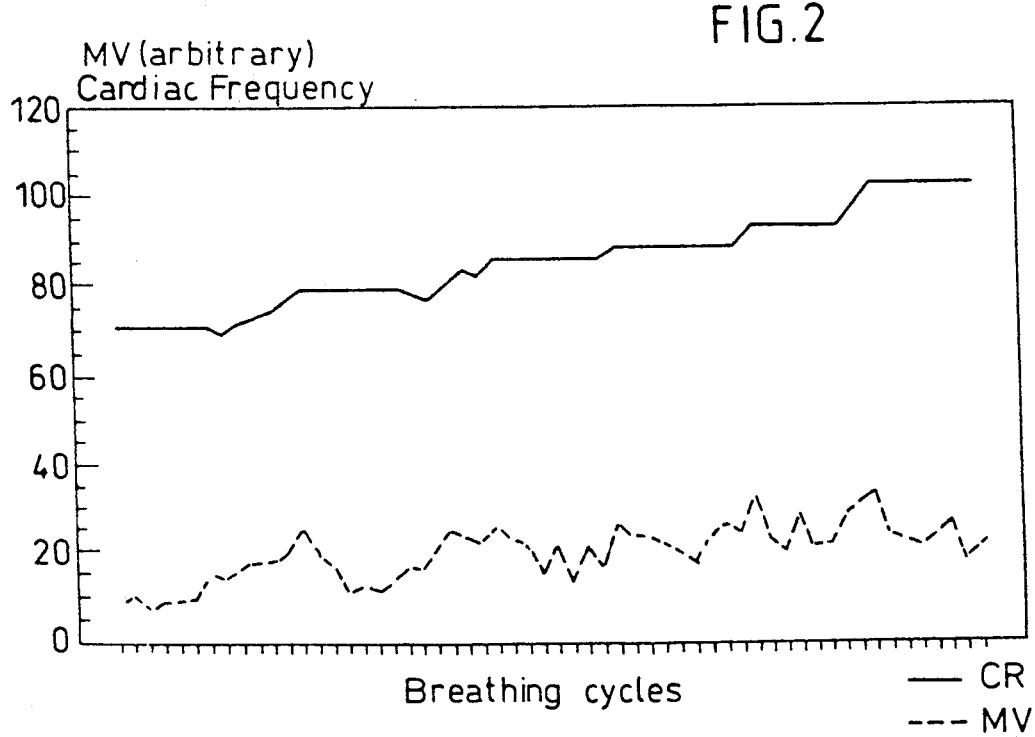
FIG. 2 is a plot comparing the minute ventilation MV plot of FIG. 1 and the calculated cardiac rate CR determined in response to minute ventilation versus breathing cycles.

As illustrated in FIG. 2, the curve CR shows a simulation of a control of the calculated cardiac rate CR according to the measured minute ventilation MV in accordance with the prior art. In spite of the presence of the ventilation gaps G during the effort, the rate response is relatively gradual. However, gaps GCR appear in the calculated cardiac rate during the rising phase of the activity level as a result of ventilation gaps G. Physiologically, the cardiac rate has only a very small variability as a function of the effort.

Advantageously, the present invention minimizes the occurrence of a decrease of the cardiac rate during a phase of effort, by distinguishing a physiological parameter from a real end of effort.

To achieve this, an analysis is made of the selected physiological parameters, namely, minute ventilation MV, and of its average values over a certain number of breathing cycles. The term "MV-4" refers to an average of the last four measured MV; the term "MV-8-0" refers to an average of the last eight measured MV; and the term "MV-8-1" refers to an average of the eight MV measured between the 9th and the 16th previous breathing cycles.

Figure 3:
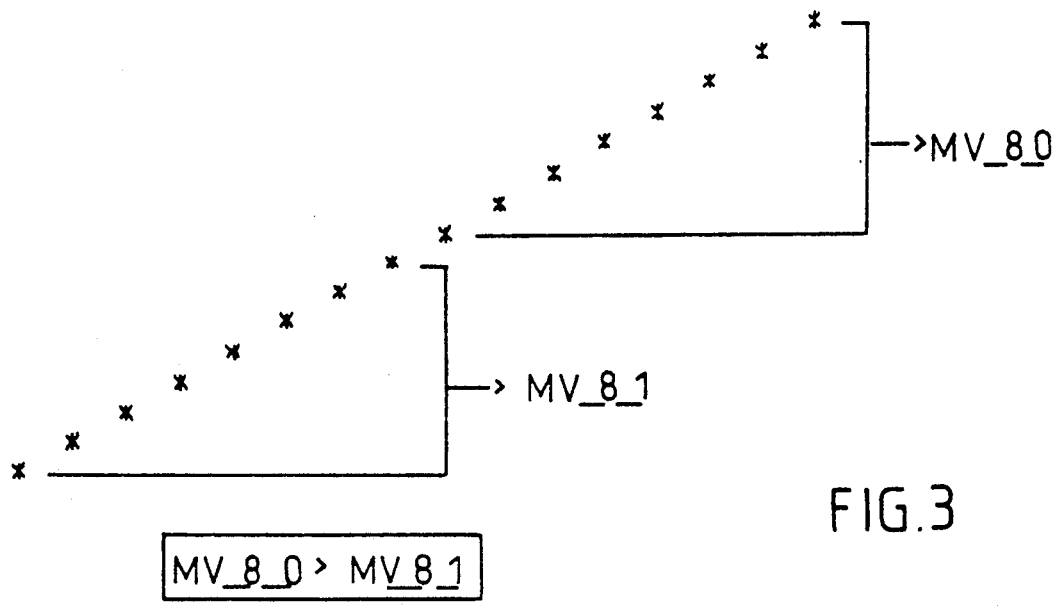
FIG. 3 is a plot representing an increasing minute ventilation MV parameter measured versus breathing cycles.
Figure 4:
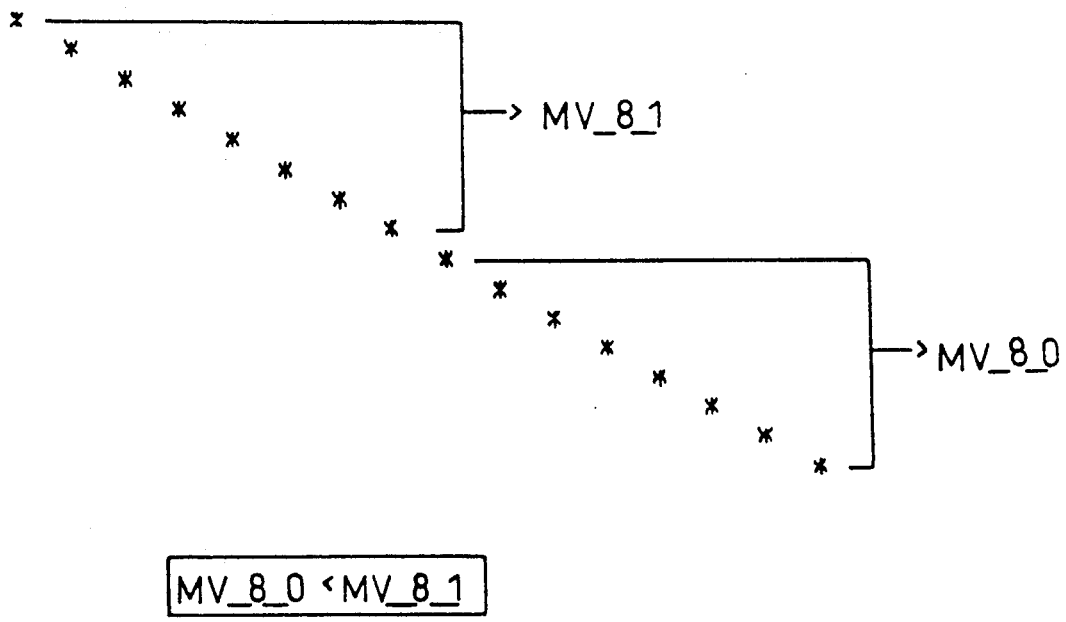
FIG. 4 is a plot representing a decreasing minute ventilation MV measured versus breathing cycles.
Figure 5:
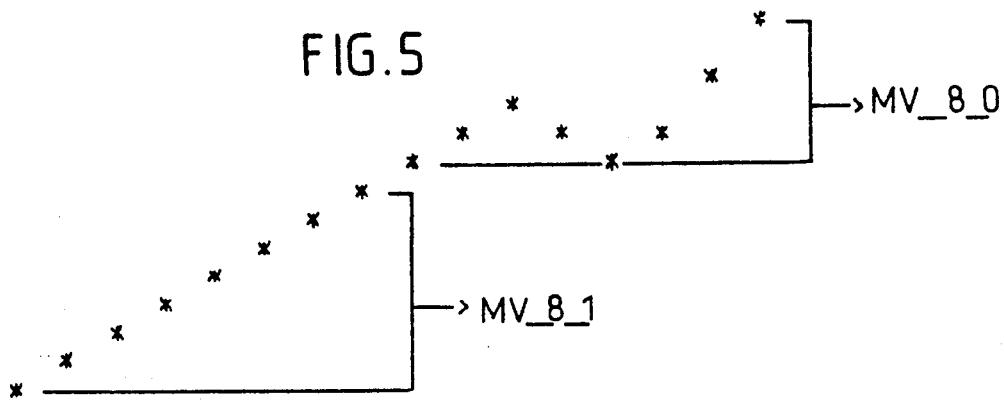
FIG. 5 is a plot representing an increasing minute ventilation MV including a ventilation gap G versus breathing cycles during an effort phase.

The principle of discriminating the ventilation gaps from an ending effort is based upon the evolution of the determined values of MV-8-0 and MV-8-1. Referring to FIG. 3, the minute ventilation parameter is shown increasing such that MV-8-0 is larger than MV-8-1. Referring to FIG. 4, the minute ventilation parameter is shown decreasing such that MV-8-0 is smaller than MV-8-1. Referring now to FIG. 5, the minute ventilation is generally increasing, and there is a ventilation gap G lasting over a few breathing cycles. However, the determined MV-8-0 remains larger than MV-8-1.

Accordingly, a relative decrease in the measure of minute ventilation during the effort phase can be identified. Consequently, by comparing the average minute ventilation over the last eight cycles with the average minute ventilation over the preceding last eight cycles, a genuine ending of an effort (MV-8-0 < MV-8-1) can be distinguished from a ventilation gap (MV-8-0 > MV-8-1).

Figure 6:
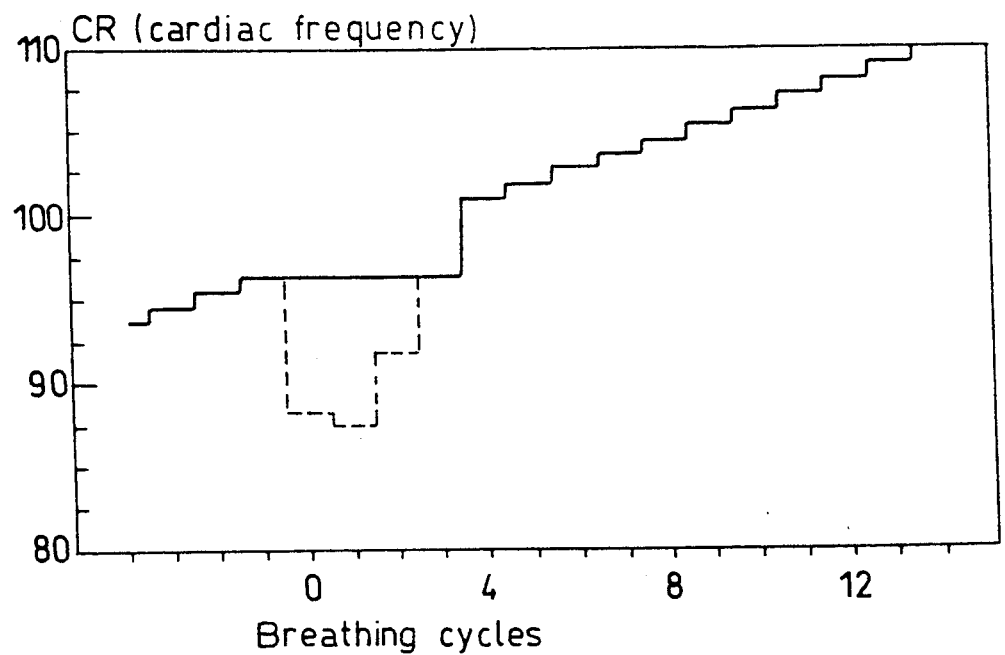
FIG. 6 is a plot comparing the applied cardiac rate ACR and the calculated cardiac rate CCR versus breathing cycles during an effort phase including a ventilation gap.

In this regard, FIG. 6 illustrates the difference between a calculated cardiac rate CCR and an applied cardiac rate ACR during an effort. The rate CCR is calculated through the control relationship with the last measured minute ventilation (or an average of a number of measures) and the rate ACR is determined in accordance with the present invention in response to the comparison of the two averages of minute ventilation over time. The calculated rate CCR thus follows the variation of the minute ventilation whereas the applied rate ACR does not follow a decrease in minute ventilation.

In the case of a ventilation gap, rate CCR decreases along the dotted line. In contrast, according to the invention, in response to either a calculated decrease in minute ventilation which may correspond to a suspected ventilation gap or a detected ventilation gap, the pacing rate becomes rate ACR which corresponds to the prior rate CCR rate calculated just before the decrease, which is maintained at that prior rate. The rate ACR then restarts its increment progression, and returns to the calculated rate CCR, as soon as the ventilation activity restarts up again. There is thus avoided a temporary decrease of the cardiac rate during a phase of effort.

The recovery phase is situated between the end of the effort phase and the return to the resting condition. During the recovery phase, the minute ventilation decreases to its basic value at the resting condition. To avoid perceiving a ventilation gap as an ending of an effort and being immediately followed by a decrease of the cardiac rate, the present invention uses the two determined average values for confirming the end of an effort when MV-8-0 becomes smaller than MV-8-1. Until the end of the effort is confirmed or until the ventilation gap ends as described above, which ever occurs first, the applied rate ACR, rather than the calculated rate CCR, is used to control the pacing rate.

Figure 7:
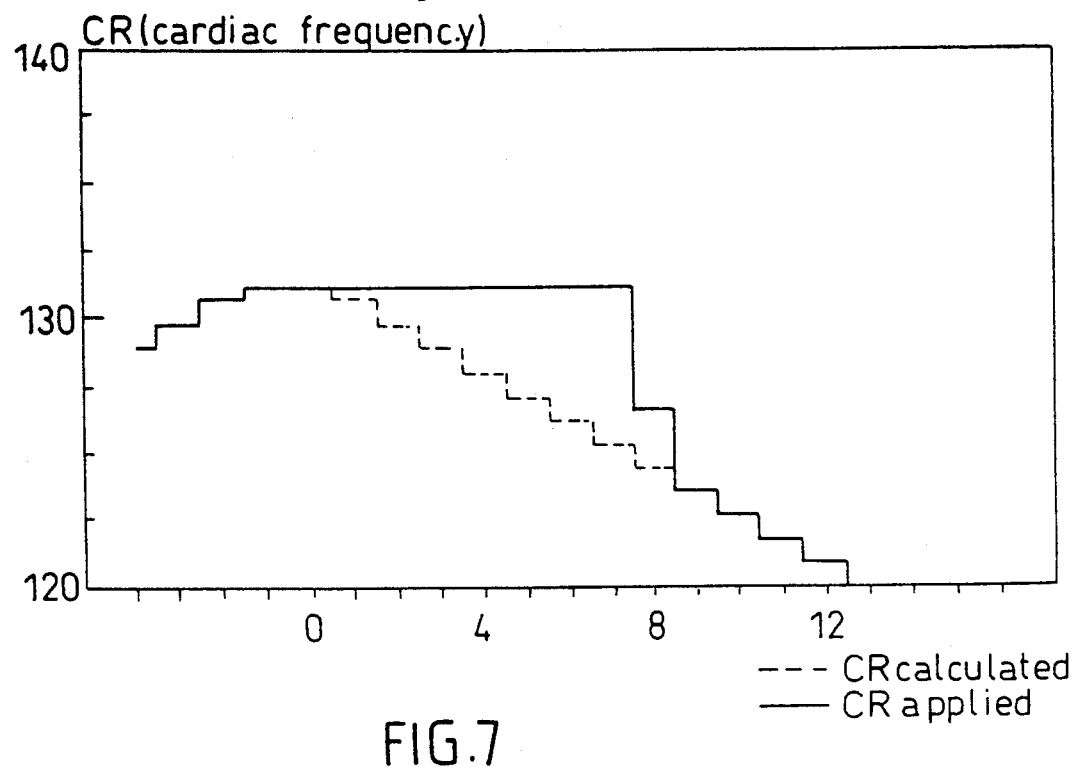
FIG. 7 is a plot a comparing the applied cardiac rate ACR and the calculated cardiac rate CCR versus breathing cycles during a recovery phase.

Referring to FIG. 7, the variations of the cardiac rate at the end of an effort phase is illustrated. The dotted line represents the rate CCR calculated through the normal control relationship. When, at the end of an effort, the minute ventilation decreases, the calculated cardiac rate CCR also is decreasing. According to the invention, in the effort phase the applied cardiac rate ACR is maintained at the last calculated value prior to the decrease until confirmation of the ending of the effort.

As soon as the end of effort is confirmed, operation switches to in the recovery phase. During the recovery phase, the pacing rate is controlled different than in the effort phase. In particular, the pacing rate is the calculated cardiac rate CCR which varies as a function of the measure of the minute ventilation parameter in accordance with the control function.

Preferably, regardless of whether the system is in an effort phase or in a recovery phase, changes in the cardiac pacing rate are limited by preselected slopes that limit the relative increase or decrease in the cardiac rate from one rate to the next. Thus there are defined an acceleration slope and a deceleration slope. These are applied in each recalculation of the cardiac rate, namely, at every four cardiac cycles. The slopes are applied over the cardiac cycle period, and are therefore expressed in milliseconds (ms).

During the recovery phase, the calculated cardiac rate is limited in its decrease by the deceleration slope. Thus, the increase in the period between successive pacing pulses will be limited by an interval corresponding to the deceleration slope. The deceleration slope period is a programmable value selected from between 16 and 94 ms, preferably 31 ms at every four cardiac cycles. Similarly, in an effort or recovery phase, the acceleration slope limits the decrease of the period between successive pacing pulses by a programmable amount selected from between 16 and 94, preferably 31 ms at every four cardiac cycles.

During the recovery phase, the sensed minute ventilation parameter is not always decreasing. A sensed increase of the ventilation may be observed, and also, therefore, an increase of the calculated heart rate. If this increase persists, it is determined that the effort is resumed, and operation changes from the recovery phase to the effort phase (see FIG. 9). On the other hand, if this increase of ventilation (and thus of the controlled cardiac rate) is merely a transient occurrence, it will then be necessary not to pass on to the effort condition (see FIG. 8). In this case, the cardiac pacing pulse rate will be the calculated cardiac rate which will increase and then decrease in response to the ventilation transient.

In accordance with the invention, if an increase in the rate CCR calculated according to the control relationship with the physiological parameter is observed, it will be authorized and, subject to the acceleration slope, be the pacing rate. If the increase occurs in the recovery mode, there will then be stored in a memory the smallest calculated cardiac rate value attained during the previous decreasing rate cycles. If the calculated cardiac rate becomes less than the stored minimal value before the 4th recalculation of the cardiac rate (each recalculation being made every four cardiac cycles), i.e., after 16 cardiac cycles, the system will then consider that it is not dealing with a restart of the effort, and it will remain in the recovery mode (see FIG. 8).

However, if at the 4th recalculation the calculated cardiac rate is still above the stored minimal value, the system will then consider that there is a restart of the effort. It will then switch over to the effort phase (see FIG. 9). This means that, in order to switch back again to the recovery phase, the above-described requirements will again have to be met, and a rate plateau will be observed prior to confirming the end of effort and returning to the recovery state.

The method for controlling the pacemaker according to the invention is implemented in the following manner:

Two functions are achieved in an asynchronous manner. First, at every four cardiac cycles, a new controlled cardiac rate is calculated, according to the ventilation information. This is performed by the metabolic demand pacemaker in the known, prior art manner. Second, at each 4th breathing cycle, a new average ventilation value will be calculated. This value and the three preceding average ventilation values are used for calculating MV-8-0 and MV-8-1.

The controlled cardiac rate CCR is calculated in accordance with a linear relationship established between the minute ventilation and the cardiac rate. Preferably, the linear relationship uses the following linear relationship, including the average value of ventilation over the last four measured values (MV-4):

$$CCR = a \times MV\text{-}4 + b;$$

wherein a and b are selected to provide a basic pacing rate when the person is in a rest condition such that a is a slope or scale parameter for correlating the relative increase of MV-4 above the rest value to an incremental cardiac pacing rate and b is the constant selected to provide the basic pacing rate corresponding to MV-4 at a resting condition. A and b are programmable in accordance with the patient's rest activity level and condition. In addition, the parameters a and b may be automatically determined and adjusted in response to ventilation information and if the average pacing rate is too low or too high over a selected time period, which determinations and adjustments form no part of the present invention.

Figure 10:
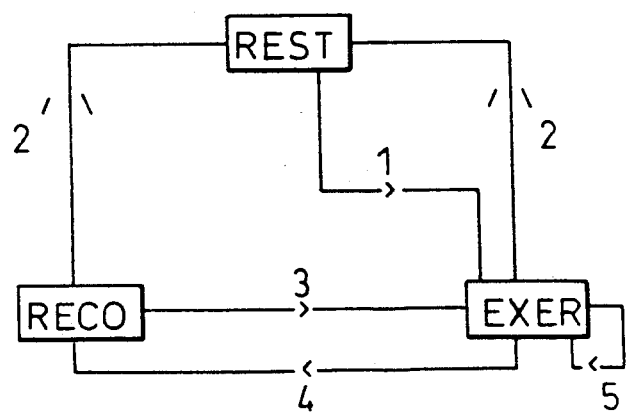
FIG. 10 is a state diagram in accordance with the present invention.

Starting from this average value MV-4 at rest, the system monitors the minute ventilation parameter and changes in MV value to determine the effort situation of the patient. Referring to FIG. 10 and the state diagram of a device in accordance with the present invention, three states are defined: rest REST, effort EXER and recovery RECO. REST corresponds to a pacing rate which is calculated to be below a selected threshold value (basic period - 6%). EXER corresponds to a pacing rate which is increasing beyond the selected threshold value. RECO corresponds to a pacing rate which is above the threshold value, but which is nevertheless decreasing.

The changes from one state to the other depend upon the outcome of certain tests about the evolution of the controlled cardiac rate. The conditions of changes of states are schematized in the diagram of states in FIG. 10 and the Table below of Functions and Transitions. In the diagram of FIG. 10, transition Tracks 1 to 5 are directional as indicated by the arrows and are defined as follows, wherein terms in quotation marks correspond to the variables used in the Table and the software listing appended to this specification as indicated.

Track 1 represents the period of time between successive stimulating pulses at the calculated cardiac rate "Present cycle per" being less than the period of time corresponding to the threshold cardiac rate "Per thr". Track 2 represents the period "Present cycle per" falling below the threshold period "Per thr". Track 2 from the RECO state to the REST state is the normal path of return to the rest state at the end of a recovery phase in response to the period of time between successive pacing pulses at the applied cardiac rate "Sensor esc per" being greater than or equal to the threshold period "Per thr" minus the period of time corresponding to the programmed deceleration slope "Prg dec slope". Track 2 from the EXER state to the REST state corresponds to the fast return to the rest state in the case of a ventilation artifact during the recovery phase as illustrated in FIG. 8. Track 3 represents a restart of the effort wherein the period "present cycle per" remains less than the stored maximum escape period between successive pacings in the recovery phase "Max sensor esc per in reco" after four cardiac recalculations, i.e., the counter "4 cycles index" is set equal to 4 (see FIG. 9). Track 4 represents the end of the effort wherein the period "resent cycle per" is less than the period "Sensor esc per" and the average MV-8-1 "Aver vent 8-1" is greater than or equal to the average MV-8-0 "Aver Vent 8-0" (see FIG. 7). Track 5 represents the criterion of the end of the effort is not met.

In the Table, the Old State category identifies the existing state, and provides separate transitions to New States, if any. The term PRESCYPER is the same as "present cycle per" corresponding to the time interval between stimulating pulses of the calculated cardiac rate; the term "PERTHR" is the same as "Per thr" and refers to the threshold cycle period corresponding in the threshold activity rate which is a function of programmed base period "Prg bas per" of the basic pacing rate; the term SENSECPER is the same as "sensor esc per" and refers to the sensed cycle period corresponding to the time interval between stimulating pulses of the applied cardiac pacing rate; the term PDESSLOPE is the same as "Prg desc slope" and is the interval of the programmed deceleration slope; the term AVERVEN81 is the same as "Aver vent 8-1" and MV-8-1; the term AVERVEN80 is the same as "Aver vent 8-0" and MV-8-0; the term MAXSENREC is the same as "Max sensor esc per in reco", the term "CYCLIND4" is the same as "4 cycle index" which is in the index to start sensor descent; the "Vent 4 stack" refers to the stack memory for acquiring the last 4 measured minute ventilation used to form the averages MV-4, MV-8-0 and MV-8-1; the term "Prg accel slope" refers to the interval of the programmed acceleration slope.

viding the selected cardiac pacing rate. A preferred device is the microprocessor of a rate adaptive metabolic demand dual chamber pacemaker having input parameters programmable for the patient's characteristics, including acceleration and deceleration slopes, in the known manner. Appropriate devices for converting analog circuit signals to digital signals and vice versa may be provided. It is to be understood, however, that the method also may be performed by analog circuit devices, and by a combination of digital and analog circuits. All of the foregoing components are conventional.

A suitable microprocessor controlled dual chamber pacemaker for use with the present invention is to one used in the model CHORUS ™ I or II, available from Ela Medical, Montrouge, France, provided that it is first modified with a sensor, circuits and signal processing algorithm to acquire the measure of minute ventila-

TABLE

| old state | INPUT | new state | B | C | F | G | H | I | J | A |
|---|---|---|---|---|---|---|---|---|---|---|
| REST | PRESCYPER < PERTHR | EXER | | C | | G | | | J | |
| | ELSE | REST | B | | | | | | | |
| EXER | PRESCYPER >=PERTHR & SENSESCPER>=PERTHR −PDESSLOPE | REST | | C | | | | | | |
| | PRESCYPER >SENSESCPER & AVERVEN81>=AVERVEN80 | RECO | | | F | | H | | | A |
| | PRESCYPER > SENSESCPER & AVERVEN81<AVERVEN80 | EXER | | | | | | | | |
| | ELSE | EXER | | | | | | | | A |
| RECO | PRESCYPER >=PERTHR & SENSESCPER>=PERTHR −PDESSLOPE | REST | | C | | | | | | |
| | PRESCYPER < MAXSENREC & CYCLIND4 = 3 | EXER | | | | | | | | A |
| | PRESCYPER < MAXSENREC & CYCLIND4 = 3 | RECO | | | | | | I | | A |
| | ELSE | RECO | | | F | | H | | | A |

The function key for the Table is as follows:
A: Calc "Sensor esc per"
B: Set "Sensor esc per" to "Prg bas per"
C: Set "Sensor esc per" to "Per thr"
F: Update "Max sensor esc per in reco"
G: Set "Index to start senor descent"
H: Ser "4 cycles index"
I: Increment "4 cycles index"
J: Update Vent 4 stack if The method of the invention is preferably performed by a computer, more preferably, an eight bit microprocessor device having software instructions in a associated memory device, an input for receiving the calculated cardiac rate based on a selected control relationship, an input of the measure of the physiological parameter, e.g., minute ventilation, and an output for protion and provided with a suitable algorithm to calculate a cardiac rate in response to the ventilation.

A preferred embodiment of a software program useful for controlling a microprocessor controlled metabolic demand dual-chambered pacemaker in accordance with the present invention is as follows (written in the program description language):

---

AVERVEN80: average of the 8 most recent ventilations
"Aver vent 8-0" =

$$\left( \sum_{i=0}^{1} \text{Vent 4 stack } ((\text{"Vent 4 ptr"} - 2 + i) \text{ modulo } 4) \right) / 2$$

AVERVEN81: average of the 8 ventilations preceding the 8 most recent ventilations
"Aver vent 8-1"=

$$\left( \sum_{i=0}^{1} \text{Vent 4 stack } ((\text{"Vent 4 ptr"} + i) \text{ modulo } 4) \right) / 2$$

CYCLIND4 = "4 cycles index"
MAXSENREC = "Max sensor esc per in reco"
PDESSLOPE = "Prg desc slope"

```
        PERTHR = "Per thr"
        PRESCYPER = "Present cycle per"
        SENSESCPER = "Sensor esc per"
Calc: "sensor esc per"
        CASE    ("Sensor esc per")
        PART    (> "Present cycle per" + "Prg accel slope")
                "Sensor esc per" = Sensor esc per" − "Prg accl slope"
        PART    (< "Present cycle per" + "Prg desc slope")
                "Sensor esc per" = "Sensor esc per" + "Prg dec slope"
        ELSE
                "SENSOR esc per" = Present cycle per"
        ESAC
        IF      "SENSOR esc per" < "prg sensor min per"
        THEN
                "Sensor esc per" = "prg sensor min per"
        ELSE
            IF      "Sensor esc per" > "prg bas per"
            THEN
                    "Sensor esc per" = "prg bas per"
            ELSE
            FI
        FI
Set     "Sensor esc per" to "Prg bas per"
        "Sensor esc per" = "Prg bas per"
Set     "Sensor esc per" to "Per thr"
        "Sensor esc per" = "Per thr"
Update "Max sensor esc per in reco"
        "Max sensor esc per in reco" = "Present cycle per"
Set     "Index to start sensor descent"
        "Index to start sensor descent" = 1024
Set     "4 cycles index"
        "4 cycles index" = 0
Increment "4 cycles index"
        "4 cycles index" = "4 cycles index" + 1
Update Vent 4 stack
        IF      "Prg calib" = 0
        THEN
                FOR i = 0 to 3
                DO
                  Vent 4 stack (("Vent 4 ptr"+i)) = "Min vent cal"
                OD
        ELSE
        FI
CASE ("Exercise state")
PART (REST)
    IF
                "Present cycle per" < "Per thr"
    THEN
                "Exercise state" = EXER
                "Sensor esc per" = "Per thr"
                "Index to start sensor descent" = 1024
                Update Vent 4 stack if
    ELSE
                "Sensor esc per" = "Prg bas per"
    FI
PART (EXER)
    IF
                AND
                        "Present cycle per" > = "Per thr"
                        "Sensor esc per" > = "Per thr" − "Prg desc slope"
                DNA
    THEN
        "Exercise state" = REST
        "Sensor esc per" = "Per thr"
    ELSE
        IF
            "Present cycle per" > "Sensor esc per"
        THEN
            "Aver vent 8-0" =
```

$$\left( \sum_{i=0}^{1} \text{Vent 4 stack} ((\text{"Vent 4 ptr"} - 2 + i) \text{ modulo } 4) \right) / 2$$

"Aver vent 8-1" =

$$\left( \sum_{i=0}^{1} \text{Vent 4 stack} ((\text{"Vent 4 ptr"} + i) \text{ modulo } 4) \right) / 2$$

```
            IF
```

```
                    "Aver vent 8-1" > "Aver vent 8-0"
        THEN
                    "Exercise state" = RECO
                    "Max sensor esc per in reco" = "Present cycle per"
                    "4 cycles index" = 0
                    Calc "Sensor esc per"
        ELSE
        FI
    ELSE
        Calc "Sensor esc per"
    FI
FI
PART (RECO)
    IF
        AND
                    "Present cycle per" >= "Per thr"
                    "Sensor esc per" >= "Per thr" - "Prg desc slope"
        DNA
    THEN
        "Exercise state" = REST
        "Sensor esc per" = "Per thr"
    ELSE
        IF
                    "Present cycle per" < "Max sensor esc per in reco"
        THEN
            IF
                        "4 cycles index" >= 3
            THEN
                "Exercise state" = EXER
            ELSE
                "4 cycles index" = "4 cycles index" + 1
            FI
        ELSE
            "Max sensor esc per in reco" = "Present cycle per"
            "4 cycles index" = 0
        IF
        Calc "Sensor esc per"
        FI
ELSE
        "Ram lsb" = 00H
ESAC
```

A preferred software code listing of a preferred embodiment for controlling a microprocessor controlled pacemaker in accordance with the invention is set forth in the software appendix.

Preparation of alternate suitable software for controlling other metabolic demand microprocessor controlled pacemakers, to operate in accordance with the present invention is believed to be well within the ability of a person of ordinary skill in the art.

One skilled in the art will appreciate that the present invention can be practiced by other than the described embodiments which are presented for purposes of illustration and not of limitation.

Figure 11:
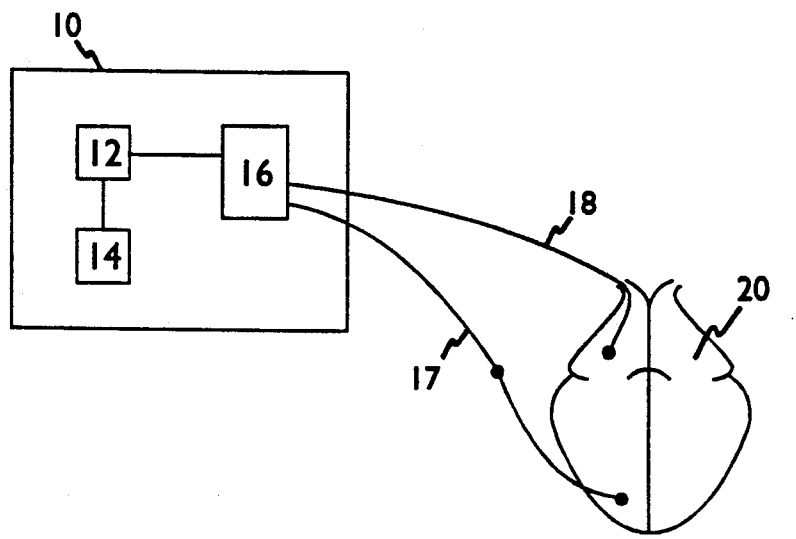
FIG. 11 is a block diagram of the apparatus of a preferred embodiment of the present invention.

Referring to FIGS. 11, 12, and 13A—13D, a preferred embodiment of the apparatus and method steps of the present invention are shown. With reference to FIG. 11, an apparatus of the present invention includes a pacemaker 10 having a microprocessor 12, memory devices 14 for containing software programming, counters, acquired and processed data and other software related parameters, and an interface circuit 16 which includes circuits for conditioning signals sensed from the heart activity and transthoracic impedance measurements, converting the sensed analog signals to digital signals for processing by microprocessor 12, and a stimulating pulse generator. Also included are cardiac leads 17 and 18 which are implanted in the patient's heart 20 for monitoring cardiac electrical activity, providing stimulating pulses, and sensing the transthoracic impedance variations from which the minute ventilation measure is derived as already described.

Figure 12:
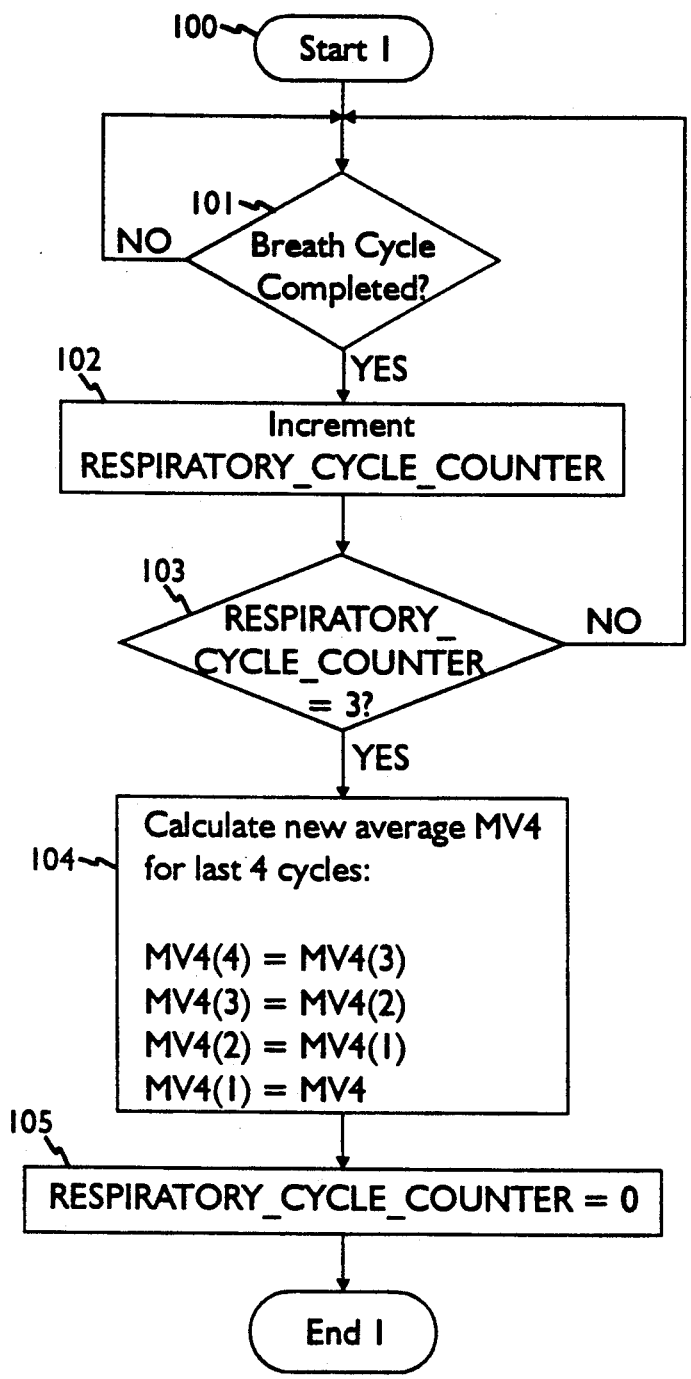
FIG. 12 is a flow chart of the transthroacic impedance processing and minute ventilation determining functions in accordance with an embodiment of the present invention.

Referring to FIG. 12, a flow chart for the processing of the transthoracic impedance data over a respiratory cycle by the microprocessor to determine a minute ventilation measure is shown. The routine starts at step 100 and first checks at step 101 whether a breathing cycle has been completed. If not, the routine waits until it has. If a breathing cycle is completed, then at step 102 the minute ventilation measure MV is calculated for that breathing cycle and a counter RESPIRATORY_CYCLE counter is incremented. This cycle counter is checked at step 104 and if it is not equal to three, meaning that four breathing cycles have not elapsed since the counter was reset, the routine passes to process further breath data at step 101. If the counter is equal to three, then a new average of the last four measured values MV is obtained at step 104 and the cycle counter is reset to 0 at step 105.

At step 104 the various minute ventilation averages are recalculated such that the new average MV4(1) (based on the last four acquired MV values for the four most recent breath cycles) is added to the prior calculated average MV4(2) for the preceding four breath cycles (the fifth to eighth preceding breath cycles). These terms are averaged to provide the parameter MV-8-0. In addition, the previously calculated averages of MV4(3) (the ninth to twelfth preceding breath cycles) and MV4(4) (the thirteenth to sixteenth preceding breath cycles) are added and averaged to provide the parameter MV-8-1. The averages MV-8-0 and MV-8-1 are used in controlling the pacing rate as described herein. Thereafter, the routine returns to Start1 at step 100 to process further breath cycle data.

Referring to FIGS. 13A-13D, a flow chart for the processing of the cardiac cycle data and acquired minute ventilation data to provide the calculated pacing rate and an applied pacing rate is shown. This routine operates asynchronously from the routine that acquires the minute ventilation parameters illustrated in FIG. 12. The routine starts at step 200 and at step 201 waits until a cardiac cycle has completed before proceeding. At step 202, a counter CARDIAC_CYCLE_COUNTER is incremented and at step 203 the routine checks whether a selected number of cardiac cycles have occurred (i.e., whether the counter CARDIAC_CYCLE COUNTER=N). If they have, then the cardiac cycle counter is reset to zero at step 204 and the routine then determines the cardiac pacing rate. This determination is made according to the patient's state of exercise and as a function of the determined average minute ventilation values MV4(n) (n=1, 2, 3, and 4) in accordance with the aforedescribed algorithm and in the following manner.

Figure 13B:
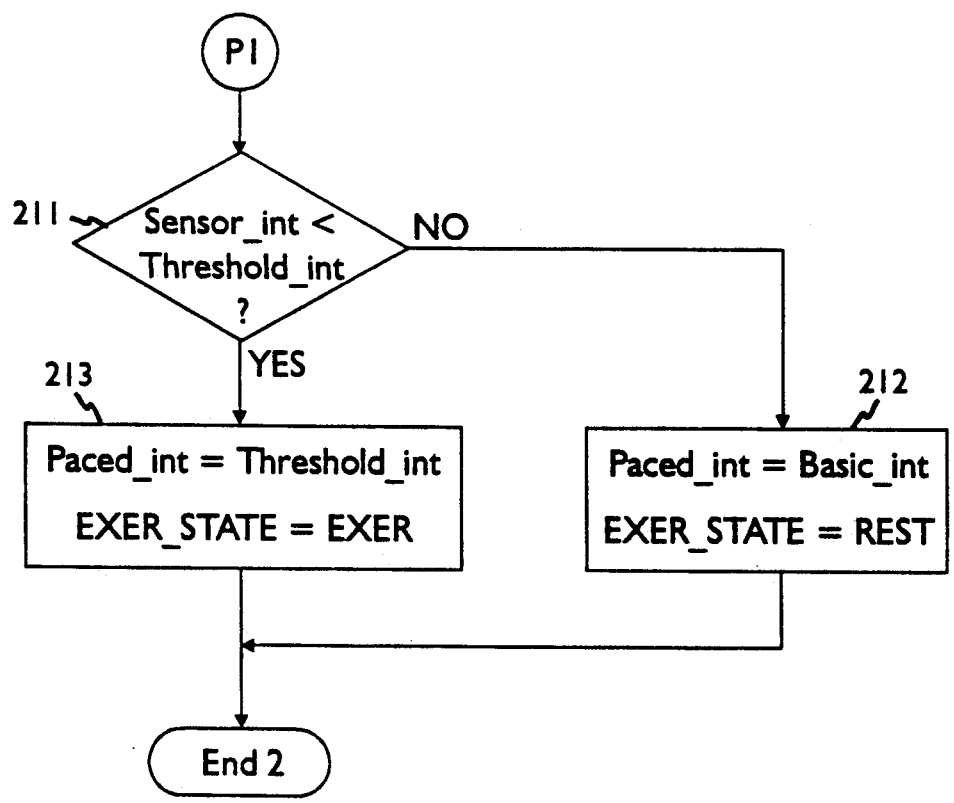
FIGS. 13A–13D are a flow chart of the pacing rate determining functions in accordance with an embodiment of the present invention.

If the patient's state is at REST as determined at step 210, the routine passes to subroutine P1, as illustrated in FIG. 13B, where the interval Sensor_int, calculated based on the calculated cardiac rate according to the algorithm $a \times MV4(1) + b$, is compared to threshold interval Threshold_int at step 211. The interval Threshold_int is set to be 6% greater than the programmed basic pacing interval Basic_int. If the interval Sensor_int is less than the interval Threshold_int, which corresponds to an increasing pacing rate, then at step 212 the interval Paced_int is set equal to the Threshold_int and the patient's exercise state is changed from rest (REST) to effort (EXER) state. If instead the interval Sensor_int is greater or equal to the Threshold_int, then at step 213 the pacing interval Paced_int is set equal to the interval Basic_int for the basic pacing rate and the patient's state is maintained in the REST state. In either case, the routine then ends and returns to step 200 to wait until the next N cardiac cycles occur and the pacing rate is recalculated.

Figure 13A:
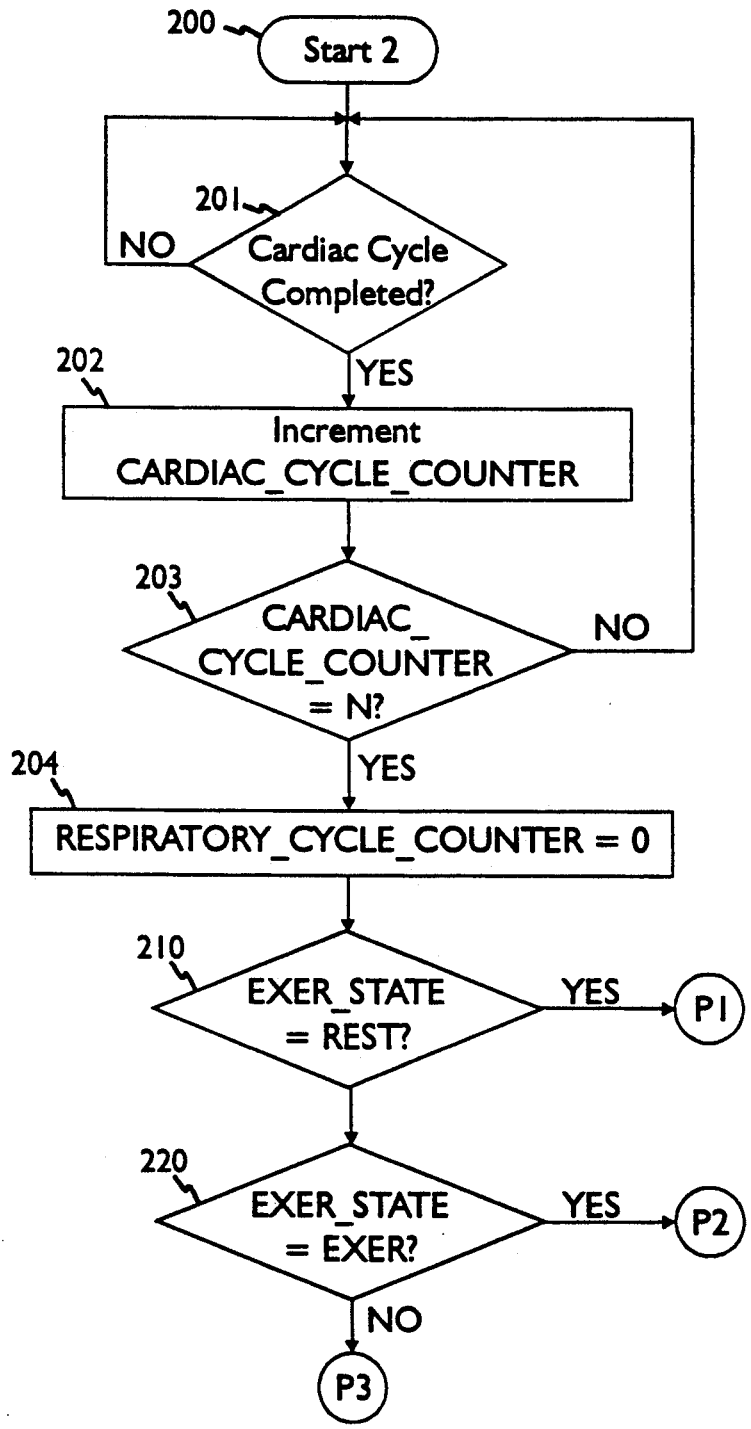
Figure 13C:
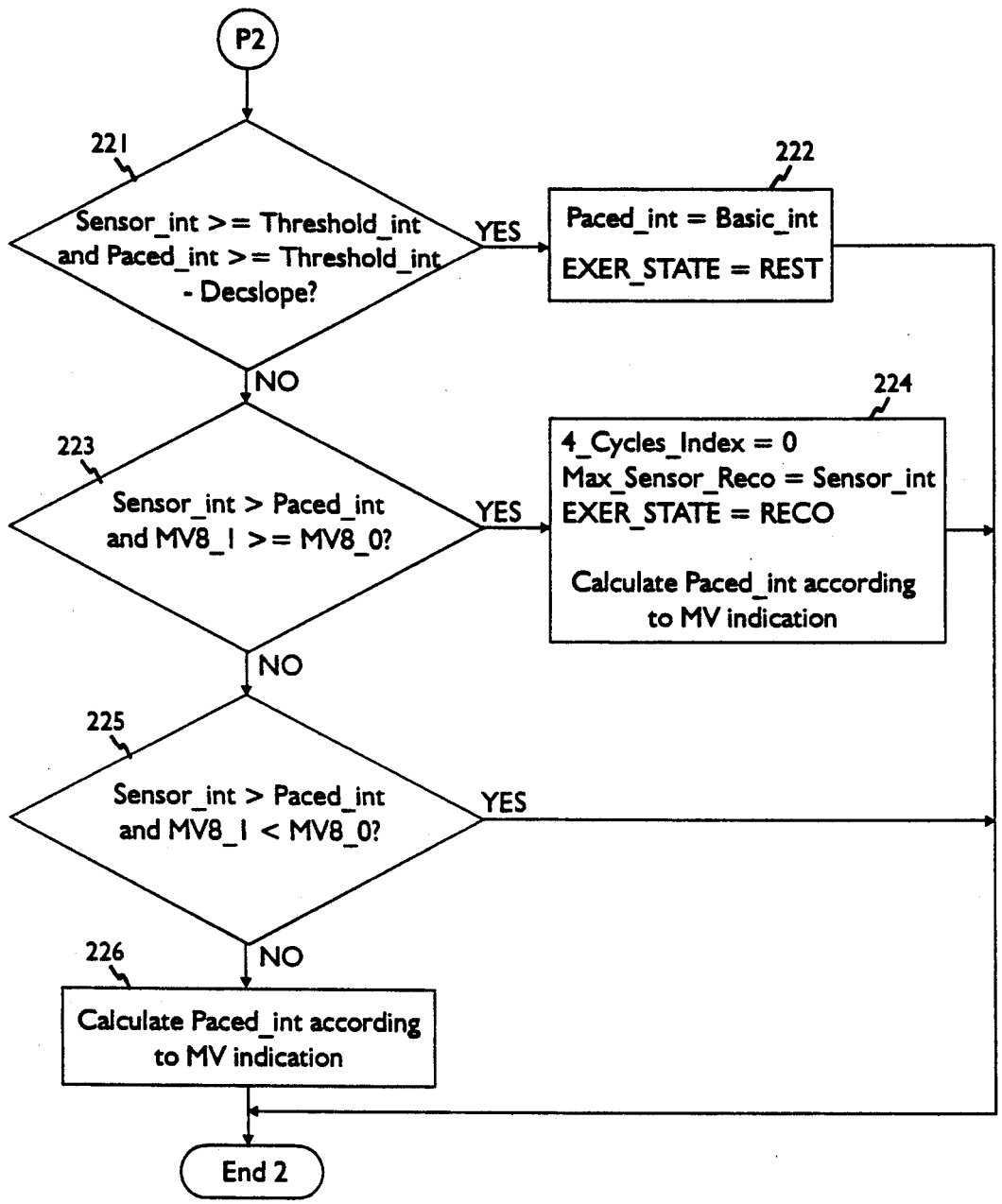

If the patient's state is in EXER as determined at step 220, the routine branches to the subroutine P2, as illustrated in FIG. 13C. At step 221 it is determined whether the calculated interval Sensor_int is greater than or equal to the threshold interval Threshold_int, and whether Paced_int is greater than or equal to the threshold interval minus the deceleration slope interval (Threshold_int - Decslope). If both conditions are true, then the routine proceeds to step 222 where the pacing interval Paced_int is set equal to Basic_int and the patient's exercise state is set to REST. The routine then ends and returns to Start2 at step 200. If both of these conditions are not true, the routine then passes to step 224 where the following occurs. A counter 4_Cycles_Index is set equal to zero, a term Max_Sensor_Reco is set equal to the Sensor_int, and the patient's exercise state is changed to recovery (RECO). Thus, these conditions indicate that the pacing rate has slowed and the end of effort, as represented by MV8_1] MV8_0, has occurred. In this case, the pacing interval Paced_int is set equal to the Sensor_int, according to the algorithm.

At step 225, the routine tests whether the patient is undergoing a decrease in ventilation which is not yet confirmed as an end of effort, namely a presumed ventilation gap. If it is, i.e., Sensor_int is greater than or equal to the Paced_int and MV8_1 is greater than or equal to MV8_0, then the Paced_int is not recalculated, Paced_int is kept at its prior value. If the conditions tested at step 225 are not true, then the minute ventilation is not effectively decreasing and the pacing interval Paced_int is calculated according to the algorithm at step 226. Thereafter, the subroutine P2 ends and returns to Start2 at step 200.

Figure 13D:
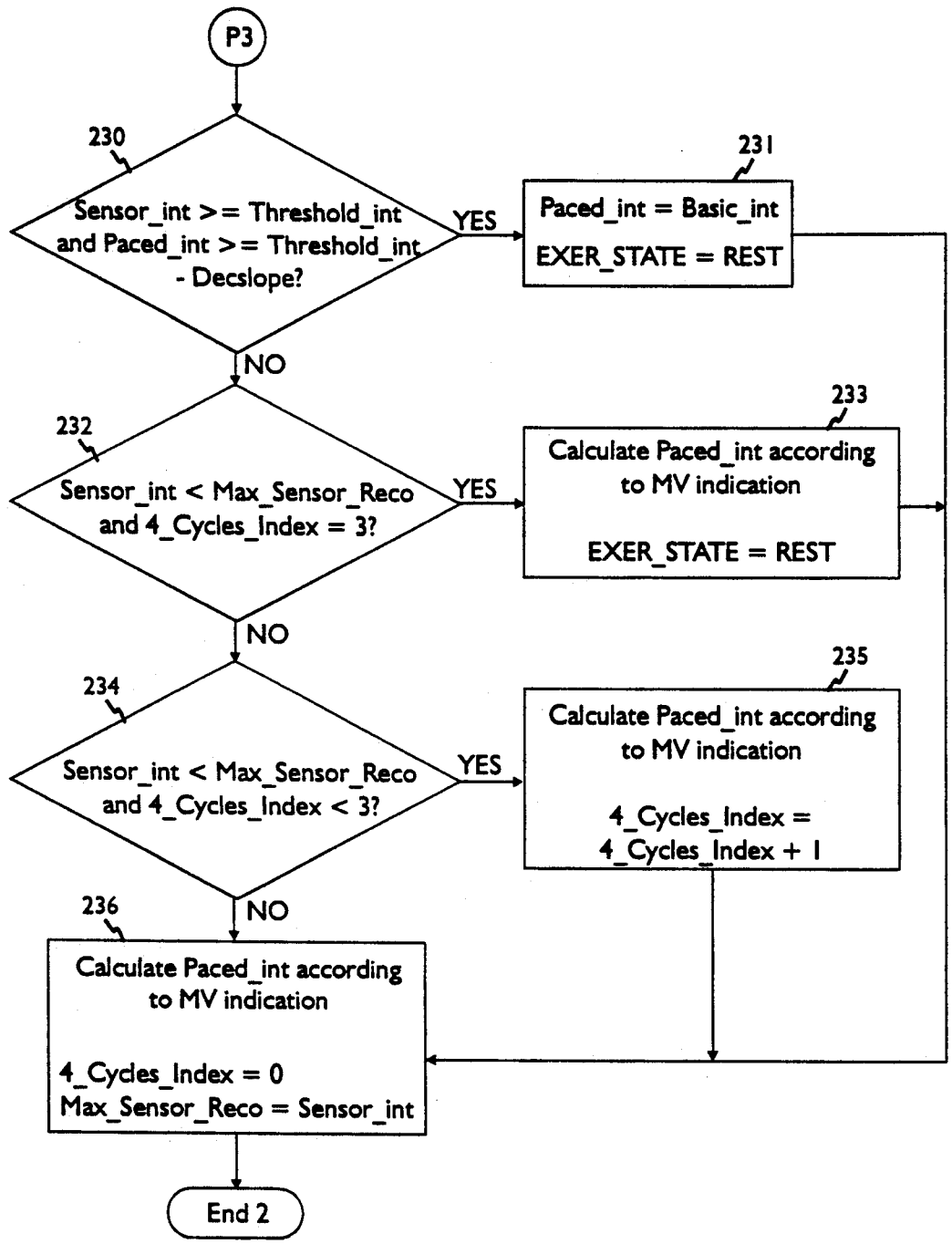

If it is determined that the patient's state is not in REST at step 210 or EXER at step 220, then it is in RECO and routine passes to subroutine P3, which illustrated in FIG. 13D. At step 230 the routine tests whether Sensor_int Threshold_int and Paced_int is greater than or equal to (Threshold_int - Decslope). If both conditions are true, the routine passes to step 231 where the Paced_int is set equal to the Basic_int and the patient's exercise state is changed to REST. If instead both conditions at step 230 are not true, the routine passes to step 232 where it is determined if the Sensor_int is less than stored value Max_Sensor_Reco and the counter 4_Cycles_Index=3. If these two conditions are true, meaning that the pacing rate according to the algorithm is greater than the prior maximum interval during the recovery state and this condition has continued for four calculated cycles, then the routine passes to step 233 where the patient's state is changed to the EXER state and the pacing rate is calculated according to the algorithm. If both conditions of step 232 are not true, then the routine passes to step 234 where it is determined if the Sensor_int is less than the Max_Sensor_Reco value and 4_Cycle_Index is less than 3. If these conditions are true, then the routine passes to step 235 where the pacing rate is calculated according to the algorithm and the counter 4_Cycles_Index is incremented. If the conditions at step 234 are not true, then the routine passes to step 236 where the passing rate is calculated according to the algorithm, the counter 4_Cycles-Index is reset to 0, and the value Max_Sensor_Reco is set equal to the Sensor_Int. Thereafter, after setting or calculating the pacing rate at steps 231, 233, 235 or 236, the routine ends and returns to Start2 at step 200 for the next series of cardiac cycles.

I claim:

1. A method of controlling a pacemaker comprising
    sensing a patient's breathing cycles, minute ventilation corresponding to the metabolic demand of the patient, and cardiac electrical activity corresponding to successive cardiac cycles;
    calculating a cardiac pacing rate once a number of cardiac cycles for a number of cardiac cycles comprised between two and ten cycles as a function of the measured minute ventilation
    calculating a first average of the minute ventilations measured over the eight last breathing cycles;
    calculating a second average of the minute ventilations measured over the previous eight last breathing cycles;
    comparing the first average to the second average;
    determining that an effort phase is present when the first average is greater than the second average and that a recovery phase is present when the first average is less than the second average; and
    applying a pacing rate as a first function of the calculated cardiac rate in response to a determined effort phase and as a second function of the calculated cardiac rate in response to a determined recovery phase.

2. A method according to claim 1, further characterized by determining relative changes in the calculated cardiac rate, identifying the occurrence of a ventilation gap in response to a determined decreasing calculated cardiac rate during a determined effort phase, and wherein the first function is further characterized by maintaining the applied pacing rate at the calculated cardiac rate prior to the occurrence of the detected ventilation gap.

3. A method according to claim 1, further characterized by determining relative changes in the calculated cardiac rate, detecting a transition from the effort phase to the recovery phase, and the first function is further characterized by maintaining the applied pacing rate at the calculated cardiac rate prior to a determined decrease of the calculated cardiac rate, and the second function is further characterized by decreasing the applied pacing rate to the calculated cardiac rate in response to a detected transition to the recovery phase.

4. The method according to claim 3, in which the step of decreasing the applied pacing rate to the calculated cardiac rate following transition to the recovery phase is characterized by providing a maximum interval between successive pacings corresponding to a selected deceleration slope, decreasing the applied pacing rate by a rate decrement following each recalculation of the cardiac rate, and limiting the rate decrement to the maximum interval.

5. A method according to claim 4, characterized by determining the minimum calculated cardiac rate during breathing cycles in a recovery phase, determining the occurrence of a ventilation artifact during the recovery phase and the number of breathing cycles said ventilation artifact lasts and remaining in the recovery phase in response to a ventilation artifact that last fewer than four breathing cycles.

6. The method of claim 1 characterized in that calculating the cardiac rate is characterized by calculating the cardiac rate once every four cardiac cycles.

7. A method of controlling the pacing rate of a cardiac pacemaker that monitors a physiological parameter indicative of metabolic demand and calculates periodically a cardiac rate as a function of a measure of the physiological parameter comprising the steps of:
(a) measuring the physiological parameter a first number of times and calculating a first average of the first number of measures of the physiological parameter;
(b) measuring the physiological parameter a second number of times and calculating a second average of the second number of measures of the physiological parameter, the first number of measures being acquired later in time than the second number of measures;
(c) determining that an effort phase is present in response to the first average being greater than the second average and that a recovery phase is present in response to the first average being less than the second average; and
(d) controlling the pacing rate by selecting the pacing rate in response to the determination of being in one of an effort phase and a recovery phase and the calculated cardiac rate.

8. The method of claim 7 where step (d) further comprises providing the calculated cardiac rate as the selected pacing rate during the recovery phase and providing an applied cardiac rate as the selected pacing rate during the effort phase.

9. The method of claim 8 wherein providing an applied cardiac rate further comprises:

(e) determining that a decreasing condition exists when one of the last acquired measured physiological parameter is less than the preceding acquired physiological parameter and the last calculated cardiac rate is less than the prior calculated cardiac rate;
(f) providing the calculated cardiac rate in response to the absence of a decreasing condition in the measured physiological parameter; and
(g) maintaining the last calculated cardiac rate as the pacing rate in response a decreasing condition, the last calculated cardiac rate being calculated before the existence of the decreasing condition.

10. The method of claim 9 wherein step (g) further comprises monitoring the transition from an effort phase to a recovery phase in response to changes in the first and second averages, and providing the calculated cardiac rate as the pacing rate in response to the occurrence of a transition from effort to recovery.

11. The method of claim 10 further comprising:
providing a pacing rate acceleration slope for limiting the rate of increase of the pacing rate and a pacing rate deceleration slope for limiting the rate of decrease of the pacing rate;
determining whether the pacing rate is increasing or decreasing; and
limiting the magnitude of change from one selected pacing rate to a different selected pacing rate by the rate acceleration slope for determined increasing rates and the rate deceleration slope for determined decreasing rates.

12. The method of claim 11 wherein providing the rate acceleration slope further comprises selecting an interval from between 16 and 94 ms and providing the rate deceleration slope further comprises selecting an interval from between 16 and 94 ms.

13. The method of claim 10 wherein the step of measuring physiological parameter further comprises measuring the minute ventilation during a breathing cycle, selecting the first number from between 2 and 32, selecting the second number from between 2 and 32, recalculating the calculated cardiac rate as a function of an average of from one to 16 minute ventilation measures every two to ten cardiac cycles.

14. The method of claim 13 wherein the first and second numbers are eight, and recalculating the cardiac rate further comprises recalculating the cardiac rate every four cycles based on an average of the last four minute ventilation measures.

15. The method of claim 8 wherein providing the calculated cardiac rate as the pacing rate during a recovery phase further comprises:
determining that an increasing condition exists when one of the last acquired physiological parameter is greater than the preceding acquired physiological parameter and the last calculated cardiac rate is greater than the preceding calculated cardiac rate;
storing a preceding minimum calculated cardiac rate in response to the onset of an increasing condition;
comparing subsequently calculated cardiac rates to the stored minimum calculated cardiac rate; and
determining that a transition to the effort phase has occurred in response to a subsequently calculated cardiac rate not being less than the stored minimum calculations and remaining in the recovery phase in response to a subsequently calculated cardiac rate being less than the stored minimum calculated cardiac rate within the third number of calculations.

16. The method of claim 15 wherein the third number is four.

17. In a pacemaker having a sensor for monitoring a physiological parameter indicative of metabolic demand and microprocessor for calculating periodically a cardiac rate based on a measure of the physiological parameter for pacing the heart by delivering stimulation pulses, apparatus for controlling the pacing rate comprising:
   means for calculating a first average of a first selected number of measures of the physiological parameter;
   means for calculating a second average of a second selected number of measures of the physiological parameter, the first number of measures being more recently acquired than the second number of measures;
   means for determining that an effort phase is present in response to the first average being greater than the second average, and a recovery phase is present in response to the first average being less than the second average; and
   means for selecting a pacing rate in response to the calculated cardiac rate, the determining means, and in response to transitions between the effort and recovery phases.

18. The apparatus of claim 17 wherein the selecting means further comprises:
   first means for providing the calculated cardiac rate as the pacing rate in response to a determined recovery phase and second means for providing an applied cardiac rate as the pacing rate in response to a determined effort phase.

19. The apparatus of claim 18 further comprising means for determining whether the measured physiological parameter is increasing or decreasing and means for determining whether the periodically calculated cardiac rate is increasing or decreasing, wherein the selecting means further comprises third means for providing the pacing rate as the calculated cardiac rate in response to the absence of a sensed decrease in the measured physiological parameter, and fourth means for providing the pacing rate as the last calculated cardiac rate in response to one of a sensed decrease in the measure of the physiological parameter and a sensed decrease in the calculated cardiac rate, the last calculated cardiac rate being calculated before the one sensed decrease.

20. The apparatus of claim 19 wherein the second providing means further comprises means for providing the applied pacing rate as the last calculated cardiac rate in response to the one sensed decrease during a determined effort phase, and as the calculated cardiac rate in response to a detected transition from an effort phase to a recovery phase.

21. The apparatus of claim 20 further comprising
   a first means for providing a rate acceleration slope for limiting the rate of increase of the pacing rate;
   a second means for providing a rate deceleration slope for limiting the rate of decrease of the pacing rate; and
   first means for limiting the magnitude of change from a first selected pacing rate to a following selected pacing rate by one of the rate acceleration slope for a detected increasing rate and the rate deceleration slope for a detected decreasing rate.

22. The apparatus of claim 21 wherein the acceleration slope providing means provides an interval selected from between 16 and 94 ms and the deceleration slope providing means provides an interval selected from between 16 and 94 ms.

23. The apparatus of claim 19 wherein the phase determining means further comprises means for determining the minimum calculated cardiac rate preceding a detecting increasing calculated cardiac rate during a determined recovery phase, a counter for counting the number of subsequently calculated cardiac rates that exceed the minimum calculated cardiac rate preceding the detecting increasing calculated cardiac rate, and means for determining that an effort phase is present in response to the counter count being greater than a third preselected number.

24. The apparatus of claim 23 wherein the third preselected number is four.

25. The apparatus of claim 22 wherein the sensor monitor a physiological parameter corresponding to a minute ventilation measured during a breathing cycle, the first number is selected from between 2 and 32, the second number is selected from between 2 and 32, and the microprocessor further comprises means for calculating cardiac rate as a linear function of an average of from 1 to 16 minute ventilation measures every two to ten cardiac cycles.

26. The apparatus of claim 25 wherein the first and second numbers are eight, the microprocessor calculating means recalculates the cardiac rate every four cycles and the average minute ventilation is an average of four breathing cycles.

27. In a method of controlling a pacemaker for distinguishing a ventilation gap from the end of an effort phase of a patient comprising the steps of:
   (a) monitoring a person's minute ventilation periodically;
   (b) calculating a first average of a first selected number of measures of minute ventilation;
   (c) calculating a second average of a second selected number of measures of minute ventilation, the first number of measures being acquired sequentially later in time than the second number of measures;
   (d) comparing the last measured minute ventilatin to the preceding measured minute ventilation;
   (e) determining that a decreasing condition exists in response to the last measured minute ventilation being less than the preceding measured minute ventilation;
   (f) comparing the first average to the second average; and
   (g) identifying a determined decreasing condition as a ventilation gap in response to the first average being greater than the second average and identifying the determined decreasing condition as an end of effort in response to the second average being greater than the first average.

28. The method of claim 27 further comprising determining that an effort phase is present in response to the first average being greater than the second average and determining that a recovery phase is present in response to the first average being less than the second average, wherein the step (g) comprises determining that a determined decreasing condition is an end of effort in response to being in the recovery phase and determining that a decreasing condition is a ventilation gap in response to being in the effort phase.

29. The method of claim 27 further comprising calculating periodically a cardiac rate as a function of the measured minute ventilation, providing a pacing rate for use in stimulating the patient's heart in the absence of spontaneous depolarization, the pacing rate being the calculated cardiac rate in the absence of a determined decreasing condition, maintaining the provided pacing rate constant at the last calculated cardiac rate in response to a determined ventilation gap, determining when the calculated cardiac rate becomes greater than the maintained constant pacing rate, and returning the pacing rate to the calculated cardiac rate in response to the calculated cardiac rate being greater than the maintained constant pacing rate.

30. The method of claim 29 wherein providing the pacing rate further comprises providing the calculated cardiac rate as the pacing rate in response to an identified end of effort.

31. The method of claim 30 wherein providing the pacing rate further comprises providing a rate acceleration slope for limiting the rate of increase in pacing rates and providing a rate deceleration slope for limiting the rate of decrease in pacing rates, and limiting the magnitude of change from one provided pacing rate to a following provided pacing rate by one of the rate acceleration slope for detected increasing rates and the rate deceleration slope for detected decreasing rates.

32. The method of claim 30 further comprising selecting the first number from between 2 and 32, selecting the second number from between 2 and 32, calculating an average of from 1 to 16 minute ventilation measures, and periodically calculating the cardiac rate every two to ten cardiac cycles based on a linear function of the averaged minute ventilation measure.

33. The apparatus of claim 32 wherein the first and second numbers are eight, and further comprising calculating the cardiac rate every four cycles and calculating an average of the average of the last four measured minute ventilations.

* * * * *

UNITED STATES PATENT AND TRADEMARK OFFICE
CERTIFICATE OF CORRECTION

PATENT NO. : 5,249,572
DATED : October 5, 1993
INVENTOR(S) : Bonnet

It is certified that error appears in the above-indentified patent and that said Letters Patent is hereby corrected as shown below:

Column 4, line 46, "transthroacic" should be "transthoracic";

Column 7, line 5, after "94" insert --ms--.

Column 8, line 57, "resent" should be --Present--;

Column 8, line 61, "is" should be --being--;

Column 9, line 14, before "Vent" insert --term--.

Column 9, line 42, in Table Key, for "G", "senor" should be "sensor";

Column 9, line 43 in Table Key "H", "Ser" should be "Set";

Column 9, line 47, "a" should be "an";

Column 10, line 14 "to" should be "the";

Column 11, line 7 "sensor" should be --"sensor--;

Column 16, line 9, after "which" insert --is--;

Column 16, line 23, "calculated" should be --calculation--;

Column 16, line 34, "passing" should be --pacing--;

Column 18, line 11, after "response" insert --to--;

Column 18, line 64, after "minimum" insert --calculated cardiac rate within a third preselected number of--;

UNITED STATES PATENT AND TRADEMARK OFFICE
CERTIFICATE OF CORRECTION

PATENT NO. : 5,249,572
DATED : October 5, 1993
INVENTOR(S) : Bonnet

It is certified that error appears in the above-indentified patent and that said Letters Patent is hereby corrected as shown below:

Column 20, line 11, "detecting" should be --detected--;

Column 20, line 18, "monitor" should be --monitors--;

Column 20, line 42, "ventilatin" should be --ventilation--;

Column 21, line 16, delete "the";

FIG. 13D, box 233, "EXER_STATE = REST" should be --EXER_STATE = EXER--.

Signed and Sealed this

Sixth Day of December, 1994

Attest:

BRUCE LEHMAN

Attesting Officer    Commissioner of Patents and Trademarks